United States Patent [19]

Tarbit

[11] Patent Number: 5,332,859
[45] Date of Patent: Jul. 26, 1994

[54] PROCESS FOR PRODUCING TETRABROMOPHTHALIC DIESTERS

[75] Inventor: Brian Tarbit, Northumberland, Great Britain

[73] Assignee: Great Lakes Chemical Europe, Ltd., Trauenfild, Switzerland

[21] Appl. No.: 970,919

[22] Filed: Nov. 3, 1992

[51] Int. Cl.$^5$ .................. C07C 67/08; C07C 67/48
[52] U.S. Cl. ................................ 560/83; 560/79; 560/91; 560/93; 560/98
[58] Field of Search .............. 560/83, 79, 98, 91, 560/93

[56] References Cited

U.S. PATENT DOCUMENTS

| | | | |
|---|---|---|---|
| 3,455,886 | 7/1969 | Versnel | 528/297 |
| 3,459,733 | 8/1969 | Byrd | 536/18.2 |
| 3,565,812 | 2/1971 | Anderson et al. | 252/182 |
| 3,585,185 | 6/1971 | Levis | 536/18.2 |
| 3,637,543 | 1/1972 | Kus et al. | 521/157 |
| 3,642,646 | 2/1972 | Marcus | 252/182 |
| 4,132,748 | 1/1979 | Arthur et al. | 525/180 |
| 4,582,926 | 4/1986 | Straehle et al. | 560/91 |
| 4,754,053 | 6/1988 | Mamuzic et al. | 560/78 |
| 4,845,266 | 7/1989 | Marx et al. | 560/91 |

OTHER PUBLICATIONS

Pape et al., "Tetrabromophthalic Anhydride in Flame-Retardant Urethane Foams", *J. Cellular Plastics*, Nov. 1968, pp. 438-442.

*Primary Examiner*—José G. Dees
*Assistant Examiner*—Vera C. Clarke
*Attorney, Agent, or Firm*—Woodard, Emhardt, Naughton, Moriarty & McNett

[57] ABSTRACT

Described is a batchwise process for producing tetrabromophthalic diester flame retardants having consistent product characteristics.

30 Claims, No Drawings

PROCESS FOR PRODUCING TETRABROMOPHTHALIC DIESTERS

BACKGROUND OF THE INVENTION

The present invention resides generally in the field of the preparation of tetrabromophthalic diesters by the reaction of tetrabromophthalic anhydride with polyhydric alcohols and with alkylene oxides.

The study of hydroxyl-terminated derivatives of tetrabromophthalic anhydride as flame retardants has been ongoing for some time now. Tetrabromophthalic anhydride (TBPA) has a high bromine content (68.9%), by which it or its derivatives impart flame retardancy to plastic systems such as urethanes, especially urethane foams.

Because diesterification of TBPA is highly difficult using conventional esterification techniques, the art has turned to a more simple method which involves reacting TBPA with a polyhydric alcohol (e.g. glycols) to form the half-ester and with an alkylene oxide such as propylene oxide or ethylene oxide to form the diester.

The product of this reaction, referred to herein as a tetrabromophthalic diester (TBP-diester) composition, is a viscous material which has traditionally been characterized by its viscosity, bromine content and hydroxyl number. The bromine content of these TBP-diester products typically falls in the range of about 25% to about 50%. Hydroxyl numbers and viscosities vary widely with the particular reactants and reaction conditions used, but it may be generally stated that lower viscosities and higher hydroxyl numbers are desired for most applications.

Perhaps just as important as the specific bromine content, hydroxyl number, and viscosity of a TBP-diester product is the ability to consistently produce a product having these values within a specified range. End-users of these TBP-diester flame retardants optimize polymeric formulations into which the TBP-diesters are incorporated based on their characterizing properties. It is thus of critical importance that the flame retardant products be of a consistent quality from batch to batch. A batch falling outside specifications will be unsuitable to end-users and, unless it can be recovered by further processing, may have to be discarded. Needless to say, this result is highly costly. Further, attempts to recover out-of-specification batches are themselves expensive, and often fail.

For further general background information on the subject, reference can be made to patent and other literature, including U.S. Pat. Nos. 3,455,886; 3,459,733; 3,585,185; 3,642,646; 3,565,812; 3,637,543; and to Pape, P. G. et al., "Tetrabromophthalic anhydride in Flame-Retardant Urethane Foams", *Journal of Cellular Plastics*, Nov., 1968.

In light of this background and a continued demand for tetrabromophthalic diesters for use as flame retardants, there exists a need for processes which may be employed to provide TBP-diesters having consistent qualities from batch to batch. The present invention addresses this need.

SUMMARY OF THE INVENTION

One preferred embodiment of the invention provides a batchwise process for producing a tetrabromophthalic diester composition while recycling solvent. This process includes the steps of preparing a first batch by reacting, in an organic solvent at a temperature up to about 150° C., tetrabromophthalic anhydride (TBPA), a $C_2$ to $C_6$ polyhydric aliphatic alcohol (PAA) and an alkaline oxide (AO) selected from the group consisting of ethylene oxide and propylene oxide. This reacting is in a PAA:AO:TBPA mole ratio of about 1.6–1.9:1-.3–1.5:1, so as to obtain a reacted mixture including the tetrabromophthalic diester composition and the organic solvent. The organic solvent is recovered from the reaction mixture by distillation, and analyzed to determine the level of its AO content. Thereafter, a second batch is prepared as above-described, wherein the organic solvent employed includes the recovered organic solvent and wherein its AO level is accounted for in achieving the PAA:AO:TBPA mole ratio. In a preferred mode of practicing this process, the reacting step is achieved by charging to a reactor all TBPA and PAA, and only about 10–50% of the AO necessary to provide the predetermined mole ratio. This charge is initially reacted, whereafter, in one or more subsequent charges, the remainder of the AO necessary to provide the predetermined ratio is charged and the resulting mixture (or mixtures where more than one subsequent charge is used) are also initially reacted. After all AO has been charged, the resulting mixture is then reacted at a temperature of about 75° C. to about 150° C. to obtain a finally reacted mixture including the tetrabromophthalic diester composition and the organic solvent. The recovering, analyzing, and further batch preparation steps then proceed as described above.

By these processes the invention provides a means to obtain a tetrabromophthalic diester composition which has consistency from batch to batch, for example, as illustrated by consistent viscosities, hydroxyl numbers, and bromine contents from batch to batch. These products can be further characterized by consistent acidity and water content from batch to batch. As a result, overall process efficiency and economy is increased, as fewer batches will fail to meet specification. Further, end-use of the TBP-diester products will be more effective since a consistent flame retardant material will be provided on a regular basis. Additional objects, advantages and preferred features of the invention will be apparent from the following description.

DESCRIPTION OF THE PREFERRED EMBODIMENT

For the purposes of promoting an understanding of the principles of the invention, reference will now be made to certain embodiments and specific language will be used to describe the same. It will nevertheless be understood that no limitation of the scope of the invention is thereby intended, such alterations, further modifications and applications of the principles of the invention as described herein being contemplated as would normally occur to one skilled in the art to which the invention relates.

As indicated above, the process of the invention involves the reaction of tetrabromophthalic anhydride with a polyhydric aliphatic alcohol and an alkylene oxide to form a tetrabromophthalic diester composition useful as a flame retardant in polymeric systems.

Polyhydric aliphatic alcohols (PAA's) for use in the invention include compounds having straight or branched alkyl chains and 2 or more -OH groups. These include, as examples, ethylene glycol, di-, tri- and tetraethylene glycol, trimethylene glycol, di- and tri- propylene glycol, butylene glycol, di- and tri-butylene glycol, 2-butene-1,4-diol, glycerol, trimethyloyl ethane, trimethyloyl propane, and the like. Diethylene glycol is a preferred PAA for use in the invention.

The tetrabromophthalic anhydride (TBPA) used in the invention preferably has a low sulfate content, e.g. preferably about 0.3% or less, and more preferably about 0.15% or less. Suitable TBPA for use in the invention may be prepared using techniques known to the literature, or may be obtained from a commercial source, for instance from Great Lakes Chemical Company, West Lafayette, Ind. Likewise, the alkylene oxide (AO) (ethylene oxide or propylene oxide) and PAA for use in the invention may prepared using known techniques or may be obtained from commercial sources.

The PAA, AO and TBPA are reacted in a PAA:AO:TBPA mole ratio of about 1.6–1.9:1.3–1.5:1.0. These ratios will provide TBPA-diester products having desirable properties in current end-use applications. More preferably, these materials are reacted in a PAA:AO:TBPA mole ratio of about 1.7–1.8:1.35–1.45:1.00.

The TBPA, PAA and AO are reacted in an organic solvent so as to form the TBP-diester. The organic solvent may be any organic solvent that is inert to the reactants employed under the conditions of the reaction. Preferably, the solvent will have a boiling point above about 100° C. in order to avoid the generation of large reaction pressures, and will usually have a boiling point in the range of about 100° to about 180° C. Aromatic solvents are preferred, for example including benzene derivatives such as benzene and substituted benzenes, i.e. benzenes having one or more substituents which are inert to the reactants. These include, for example, benzenes substituted with one or more alkyl groups, halogen groups or the like. Representative of these substituted benzene solvents are toluene, xylene, mono- and di-chlorobenzene, etc.

The reaction is conducted at a temperature so as to form the diester compound but so as to avoid temperatures that would cause a carboxyl-hydroxyl reaction. This result will be readily accomplished by those ordinarily skilled in the art. Generally, the reaction is conducted at temperatures up to about 150° C., more typically of about 40° C. to about 150° C.

In conducting the reaction, it is preferred to initially charge the TBPA, PAA and the organic solvent to a reactor. In doing so, it is preferred to first charge the TBPA and solvent, and to neutralize the acidity of the TBPA by adding a basic substance, e.g. KOH, prior to charging the PAA. The TBPA and PAA may then be completely reacted to form the half-ester prior to the addition of any AO. However, preferably, a portion of the AO is also initially charged to the reactor. The resulting reaction mixture is then heated to initially react the materials in the reactor, during which one or more exotherms may be observed. After this initial reacting, one or more additional charges of the AO are made, and similar application of heat will initially react the mixture(s) and cause additional exotherms. Overall, during this initial stage of the process, the addition of further amounts of AO and application of heat are conducted preferably so as to maintain the reaction temperature below about 150° C., and more preferably below about 120° C. The reaction may be cooled, if necessary, to maintain the desired temperature.

After all of the AO is in the system and the initial reacting is finished, the reaction mixture is then preferably heated and controlled at a reaction temperature of about 75° C. to about 150° C., more preferably about 90° C. to about 130° C., and most preferably about 100° C. to about 120° C. The duration of the reacting may vary widely, but is in general sufficiently long to substantially react the charged reactants to form the desired TBP-diester product. The progress of the reaction may be monitored, for instance, by periodically sampling the reaction mixture and determining the acid number of the product. Preferably, the reaction is continued at the reaction temperature until the product acid number is less than about 0.5 mgKOH/g, more preferably less than about 0.2 mgKOH/g. Usually, this reaction period will be greater than about 1 hour, typically in the range of about 1 to 10 hours, and more typically about 2 to about 5 hours.

After the reaction is complete, the reacted mixture, containing the TBP-diester product and the organic solvent, is stripped of the organic solvent, for example under vacuum at elevated temperatures. For this purpose, conventional techniques and equipment may be employed. For instance, in applicant's work, the organic solvent has been stripped from the product under vacuum (e.g. about 50 to about 10 mm hg) at a temperature above 50° C. and usually in the range of about 50° C. to about 150° C., preferably in the range of about 90° to about 130° C., and most preferably about 100° to about 120° C. Water may optionally be introduced slowly to the reaction product during the solvent strip, and residual solvent steam stripped, preferably to less than about 0.5% in the remaining product, more preferably to less than about 0.1% in the product.

The stripped organic solvent is recovered for use in preparing a subsequent batch of TBP-diester. Of course, any water from a steam stripping step is separated from the organic solvent prior to re-use. Further, the recovered organic solvent is analyzed, for example by quantitative gas-liquid chromatography (GLC) or other means, to determine its AO content. Typically, the recovered organic solvent will contain from about 1% to about 10% AO, although this figure may vary in accordance with the stripping procedure employed and other factors related to the previous batch. After determination of its AO content, the recovered organic solvent, alone or in conjunction with fresh organic solvent, can be used in the preparation of subsequent TBP-diester batches, while taking into account its AO content in achieving the desired mole ratios of PAA:AO:TBPA reactants. For example, the AO content of the recovered solvent may be accounted for by determining the amount of AO charged as a part of the recovered solvent, and subtracting this amount from the AO charge that would be needed to achieve the desired mole ratio if it were not for the AO content of the solvent (e.g. if fresh solvent were to be used).

Desirable TBPA-diester products will have hydroxyl numbers of about 150 to about 250, more preferably about 200 to about 235. Bromine contents of the products are preferably above about 45%, and typically fall in the range of about 45% to about 50%. Advantageous products have viscosities (at 60° C.) of about 5000 centipoise (cps) or less, and more desirably about 2500 cps or less, e.g. about 800 to about 2400 cps. Preferred product acid numbers are about 0.2 mg KOH/g or less and preferred water contents are about 0.15% or less.

In use, the TBP-diester compositions may be conventionally employed to prepare urethane or other flame retarded polymeric materials. As one example, the TBP-diester composition can be included in polyurethane foams in fire retardant amount. Typically in this regard, the TBP-diester compound will be included in the foam in the range of about 20 to about 30% by weight, or otherwise in sufficient amount to provide an overall bromine content of the foam of about 10 to about 15%.

The following examples are provided by way of illustration, and should not be interpreted as limiting of the invention in any way. Unless otherwise indicated, percentages given herein are percentages by weight.

EXAMPLES 1-6

A number of runs were conducted on the plant-scale which demonstrated the ability of the inventive process to produce TBP-diester products of consistent quality. These runs were conducted according to the following general procedure: A 6,300 liter glass-lined stirred reactor with a safe working pressure of 90 psi was set up for vacuum distillation, heating, cooling, temperature recordal, and vented to a caustic scrubber. Toluene (1,800 kg) was charged to the reactor, whereafter TBPA (4,545 kg) (Great Lakes Chemical Corp., West Lafayette, Ind.) was slurried into the toluene. KOH was charged to the reactor in 1.2 times the amount sufficient to neutralize the $H_2SO_4$ in the TBPA. The reactor was then sealed and pressurized to 40 psig with $N_2$ to check for leaks. After insuring no leaks in the reactor, the $N_2$ pressure was released. Diethylene glycol (DEG) (1,477 kg) was quickly charged to the reactor. After this, 250 kg of PO were charged to the reactor, and the reaction was heated to 40° C. An exotherm began and after the reaction temperature reached 60° C., cooling was applied via a water jacket on the reactor. The exotherm caused the temperature of the reaction to rise to 80° to 90° C. during this period. After the reaction temperature leveled off, an additional 756 kg of PO, representing the remainder of the PO needed to achieve the desired mole ratio, was charged over approximately 1 hour while keeping the pressure in the reactor below about 28 psi and the temperature below about 105° C. When the PO addition was complete, steam was used to hold the reactor at a temperature of about 105° to 110° C. After the reaction had been held at this temperature for 1 hour, periodic sampling and analysis of the product was begun. The reaction was continued at this temperature until the acid number of the sampled product was less than about 0.2 (mgKOH/g product). Typically, this acid number range was reached after reacting for about 3 hours at 105° to 110° C.

After the product demonstrated an acid number of less than about 0.2, the application of heat to the reactor was discontinued. The reactor was vented to the caustic scrubber while insuring no product was carried over during the venting period. Once the pressure had reached 0 psi, vacuum was applied carefully to strip off the toluene into the toluene receiver at a pot temperature of about 120° C. Distillation began at low vacuum, and the vacuum was increased slowly to maintain a good rate of distillation. After the distillation had slowed, water was run into the reaction vessel at a rate of about ½ liter per minute. The contents of the reactor were sampled for toluene beginning two hours after beginning the water addition. The reactor contents were thereafter sampled hourly until the toluene content was less then about 0.1%, whereupon water addition was discontinued. The reactor was then cooled to about 85° C., the vacuum released with $N_2$, and a final product sample was taken for analysis.

The toluene from the toluene receiver (after draining off the water) was then transferred to a vessel and sampled to determine its PO content. Afterwards, the toluene was used in a subsequent batch, with fresh toluene added to make up the 1800 kg of toluene. Five consecutive batches were run in this fashion. The results are shown in Table 1 below. The shown viscosities were determined by a Brookfield viscometer or its equivalent. The bromine contents were determined by the well-known Schoniger oxidation method. The hydroxyl numbers were determined by the known method involving esterification of phthalic anhydride comprising the modified ASTM D1638 procedure.

TABLE 1

| BATCH | 009 | 010 | 011 | 012 | 014 | 015 |
|---|---|---|---|---|---|---|
| Total Solvent Charged: | | | | | | |
| Amount (Kg): | 1800 | 1800 | 1800 | 1800 | 1800 | 1800 |
| AO Content (wt %): | 0 | 5.6 | 8.3 | 1.1 | 0 | 2.4 |
| Moles AO: | 0 | 1.7 | 2.6 | 0.3 | 0 | 0.7 |
| Fresh DEG Charged: (Moles) | 14.15 | 14.15 | 14.15 | 14.15 | 14.15 | 14.15 |
| Total AO Charged: (Moles) | 18.07 | 18.07 | 18.07 | 18.07 | 18.07 | 18.07 |
| Product Characteristic | | | | | | |
| VISCOS/60° C. | 1500 | 1600 | 1600 | 1500 | 1500 | 1200 |
| VISCOS/25° C. (*1000) | 87.1 | 93.6 | 93.2 | 88.2 | 85.0 | 61.0 |
| HYDROXYL NO. | 216 | 217 | 218 | 211 | 212 | 219 |
| ACIDITY (mgKOH/g) | 0.10 | 0.09 | 0.03 | 0.09 | 0.03 | 0.10 |
| WATER (%) | 0.13 | 0.06 | 0.12 | 0.06 | 0.06 | 0.09 |
| BROMINE (%) | 47.9 | 49.8 | 45.2 | 45.3 | 46.1 | 46.4 |

As can be seen, batches 1-6 show excellent consistency as to viscosity, hydroxyl number, acidity, and water and bromine content.

While the invention has been illustrated and described in detail in the foregoing description, the same is to be considered as illustrative and not restrictive in character, it being understood that only the preferred embodiments have been shown and described and that all changes and modifications that come within the spirit of the invention are desired to be protected.

What is claimed is:

1. A batchwise process for producing a tetrabromophthalic diester composition while recycling solvent, comprising:
   (a) preparing a first batch by reacting, in an inert organic solvent at a temperature in the range of up to about 150° C., tetrabromophthalic anhydride (TBPA), a $C_2$ to $C_6$ polyhydric aliphatic alcohol (PAA) and an alkylene oxide (AO) selected from tile group consisting of ethylene oxide and propylene oxide, said reacting being in a PAA:AO:TBPA mole ratio of 1.6-1.9:1.3-1.5:1, so as to obtain a reacted mixture including the tetrabromophthalic diester composition and the organic solvent;
   (b) recovering the organic solvent from the reaction mixture by distillation;
   (c) analyzing the recovered organic solvent to determine the level of its AO content;
   (d) preparing a second batch by repeating step (a) above wherein the organic solvent used includes the recovered organic solvent from the previous batch and wherein its determined AO level is accounted for in achieving the PAA:AO:TBPA mole ratio.

2. The process of claim 1 wherein said reacting includes reacting at a temperature of about 90° C. to about 130° C.

3. The process of claim 1 wherein the solvent is an aromatic solvent.

4. The process of claim 1 wherein the AO is propylene oxide.

5. The process of claim 1 wherein the PAA is diethylene glycol.

6. The process of claim 2 wherein said reacting includes reacting at a temperature of about 100° C. to about 120° C.

7. The process of claim 3 wherein the solvent is a benzene derivative.

8. The process of claim 6 wherein the solvent is selected from the group consisting of benzene, toluene, xylene, and chlorinated benzenes.

9. The process of claim 8 wherein the AO is propylene oxide and the PAA is diethylene glycol, and wherein the solvent is toluene.

10. The process of claim 9 wherein the PAA:AO:TBPA mole ratio in steps (a) and (d) is about 1.7-1.8:1.-35-1.45:1.00.

11. A batchwise process for producing a tetrabromophthalic diester composition while recycling solvent and so as to obtain a consistent composition from batch to batch, comprising:
   (a) preparing a first batch by reacting, in an inert organic solvent, tetrabromophthalic anhydride (TBPA), a $C_2$ to $C_6$ polyhydric aliphatic alcohol (PAA) and an alkylene oxide (AO) selected from the group consisting of ethylene oxide and propylene oxide, said reacting being in a predetermined PAA:AO:TBPA mole ratio in the range of 1.6-1.9:1.3-1.5:1 and being accomplished by:
      (i) charging to a reactor all TBPA and PAA and only a portion of the the AO necessary to provide the predetermined ratio, and heating and initially reacting this charged mixture to form an initially reacted mixture;
      (ii) charging, in one or more subsequent charges, the remainder of the AO necessary to provide the predetermined ratio and heating and reacting the resulting mixture;
      (iii) after all AO necessary to provide the predetermined ratio has been charged, reacting the resulting mixture at a temperature of about 75° C. to about 150° C. so as to obtain a finally reacted mixture including the tetrabromophthalic diester composition and the organic solvent;
   (b) recovering the organic solvent from the finally reacted mixture by distillation;
   (c) analyzing the recovered organic solvent to determine the level of its AO content;
   (d) preparing a second batch by repeating step (a) above wherein the organic solvent used includes the recovered organic solvent and wherein its determined AO level is accounted for to ensure that essentially the same PAA:AO:TBPA molar ratio is reacted in preparing the first and second batches.

12. The process of claim 11 wherein in step (a)(i) 10-50% of the the AO necessary to provide the predetermined ratio is charged and wherein said reacting in step (a)(iii) is at a temperature of about 90° C. to about 130° C.

13. The process of claim 11 wherein the solvent is an aromatic solvent.

14. The process of claim 11 wherein the AO is propylene oxide.

15. The process of claim 11 wherein the PAA is diethylene glycol.

16. The process of claim 12 wherein said reacting in step (a)(iii) is at a temperature of about 100° C. to about 120° C.

17. The process of claim 13 wherein the solvent is a benzene derivative.

18. The process of claim 16 wherein the solvent is selected from the group consisting of benzene, toluene and xylene.

19. The process of claim 18 wherein the AO is propylene oxide and the PAA is diethylene glycol, and wherein the solvent is toluene.

20. The process of claim 19 wherein the PAA:AO:TBPA mole ratio in steps (a) and (d) is about about 1.7-1.8:1.35-1.45:1.00.

21. A batchwise process for producing a consistent tetrabromophthalic diester composition, comprising:
   (a) reacting tetrabromophthalic anhydride (TBPA), diethylene glycol (DEG) and propylene oxide (PO) in an inert aromatic solvent in a DEG:PO:TBPA mole ratio of about 1.6-1.9:1.3-1.5:1 to obtain a reacted mixture including the tetrabromophthalic diester composition and the aromatic solvent;
   (b) recovering the aromatic solvent from the reacted mixture by distillation;
   (c) determining the PO content of the recovered aromatic solvent;
   (d) repeating step (a) wherein the aromatic solvent used includes the recovered aromatic solvent and wherein its PO content is accounted for in achieving the DEG:PO:TBPA mole ratio.

22. The process of claim 21 wherein said reacting is at a temperature in the range of up to about 150° C.

23. The process of claim 21 wherein the solvent is selected from the group consisting of benzene, toluene and xylene.

24. The process of claim 21 wherein said reacting is continued until the diester composition has an acid number less than about 0.2 mgKOH/g.

25. The process of claim 22 wherein said reacting includes reacting at a temperature of about 90° C. to about 130° C.

26. The process of claim 23 wherein the solvent is toluene.

27. The process of claim 25 wherein the solvent is toluene.

28. The process of claim 27 also including the step of steam stripping the reacted product to a toluene content of less than about 0.5% by weight.

29. The process of claim 27 wherein the DEG:PO:TBPA mole ratio in steps (a) and (d) is about 1.7-1.8:1.-35-1.45:1.00.

30. The process of claim 29 also including the step of steam stripping the reacted product to a toluene content of less than about 0.5% by weight.

* * * * *

UNITED STATES PATENT AND TRADEMARK OFFICE
CERTIFICATE OF CORRECTION

PATENT NO. : 5,332,859

DATED : July 26, 1994

INVENTOR(S) : Brian Tarbit

It is certified that error appears in the above-indentified patent and that said Letters Patent is hereby corrected as shown below:

In column 6, line 53, delete "tile" and insert in lieu of thereof --the--.

Signed and Sealed this

Third Day of January, 1995

Attest:

BRUCE LEHMAN

Attesting Officer     Commissioner of Patents and Trademarks